United States Patent [19]

Kishita et al.

[11] Patent Number: 5,403,945
[45] Date of Patent: Apr. 4, 1995

[54] CYCLOTRISILOXANE AND PROCESS FOR PRODUCING THE SAME

[75] Inventors: Hirofumi Kishita, Annaka; Kouichi Yamaguchi; Kenichi Fukuda, both of Takasaki; Nobuyuki Kobayashi, Annaka, all of Japan

[73] Assignee: Shin-Etsu Chemical Co., Ltd., Tokyo, Japan

[21] Appl. No.: 147,486

[22] Filed: Nov. 5, 1993

[30] Foreign Application Priority Data

Nov. 6, 1992 [JP] Japan .................................. 4-322771
Jan. 29, 1993 [JP] Japan .................................. 5-034270

[51] Int. Cl.⁶ .............................................. C07F 7/08
[52] U.S. Cl. .............................................. 556/460
[58] Field of Search ..................................... 556/460

[56] References Cited

U.S. PATENT DOCUMENTS

| | | | |
|---|---|---|---|
| 2,849,473 | 8/1958 | Bailey et al. | 556/460 |
| 3,269,984 | 8/1966 | Vaughn | 556/460 X |
| 3,398,173 | 8/1968 | Goossens | 556/460 |
| 4,060,537 | 11/1977 | Maass et al. | 556/460 |
| 4,719,024 | 1/1988 | Speier et al. | 556/460 X |
| 5,241,097 | 8/1993 | Zupancic et al. | 556/460 |

FOREIGN PATENT DOCUMENTS 0418568  3/1991  European Pat. Off. ............ 556/460

OTHER PUBLICATIONS

Chemical Abstracts, vol. 26, No. 2, Jan. 25, 1960, AN-5939b.
Chemical Abstracts, vol. 72, No. 15, Apr. 13, 1970, AN-79153v.
Chemical Abstracts, vol. 116, No. 12, Mar. 23, 1992, AN-107073s, Y. Mizutani, et al., JP-A-3192126, Aug. 22, 1991.
Chemical Abstracts, vol. 117, No. 6, p. 52, Aug. 10, 1992, AN-49941f, Y. Mizutani, et al., JP-A-413769, Jan. 17, 1992.

*Primary Examiner*—Paul F. Shaver
*Attorney, Agent, or Firm*—Oblon, Spivak, McClelland, Maier & Neustadt

[57] ABSTRACT

A cyclotrisiloxane represented by the general formula (1):

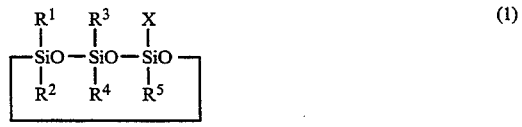

wherein $R^1$, $R^2$, $R^3$, $R^4$ and $R^5$ may be the same or different and are each an alkyl group of 1 to 3 carbon atoms and X is a cyclohexyl group or an alkyl group expressed by the formula:

$$-C_nH_{2n+1}$$

where n is an integer of 4 to 15. The cyclotrisiloxane is useful as an intermediate for producing silicone oils and silicone rubbers, and the obtained silicone oils and silicone rubbers are excellent in lubricity.

2 Claims, 3 Drawing Sheets

CYCLOTRISILOXANE AND PROCESS FOR PRODUCING THE SAME

BACKGROUND OF THE INVENTION

1. Field of the Invention

The present invention relates to a cyclotrisiloxane useful as a raw material for silicone oils and silicone elastomers which are used for greases, cosmetics, sealing materials, paints, various rubber materials and the like, and to a process for producing the same.

2. Description of the Prior Art

The below-mentioned cyclotrisiloxane, provided by the present invention, is not known.

In U.S. Pat. No. 4,898,958 the following organosilicon compound is disclosed:

An organosilicon compound represented by general formula (I):

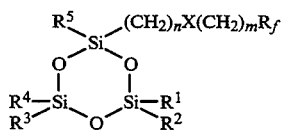

wherein $R^1$ $R^2$ $R^3$ $R^4$ and $R^5$ may be the same or different and each represent an alkyl group having 1 to 4 carbon atoms; $R_f$ represents $-C_lF_{2l+1}$ where l represents an integer of 3 to 10,

where q represents an integer of 1 to 5, or

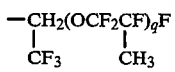

where q is as defined above; and X represents $-O-$ or $-CH_2-$; provided that n is 3 and m is an integer of 0 to 2 when X represents $-O-$, and n is 0 and m is 1 when X represents $-CH_2-$.

This compound is described to be useful for preparing silicone polymers having a high thermal resistance, chemical resistance and weathering resistance and have a small surface energy.

SUMMARY OF THE INVENTION

The task of the present invention is to provide a novel cyclotrisiloxane, and more particularly a cyclotrisiloxane having a cyclohexyl group or a $C_4$–$C_{15}$ alkyl group in the molecule.

The present invention provides a cyclotrisiloxane represented by the general formula (1):

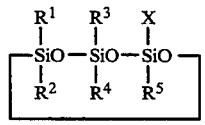

wherein $R^1$, $R^2$, $R^3$, $R^4$ and $R^5$ may be the same or different and are each a substituted or unsubstituted alkyl group of 1 to 3 carbon atoms and X is a cyclohexyl group or an alkyl group expressed by the formula:

$-C_nH_{2n+1}$ wherein n is an integer of 4 to 15.

The organosilicon compound of the present invention represented by the above general formula (1) has a structural feature that a cyclohexyl or $C_4$–$C_{15}$ alkyl group is linked to only one silicon atom among the three silicon atoms forming the cyclotrisiloxane skeleton, and this is considered to bring about various advantages.

Similarly to conventionally known hexamethyltrisiloxane, the cyclotrisiloxane undergoes readily a ring-opening polymerization in the presence of an alkali catalyst such as, e.g., KOH, (n-$C_4H_9$)$_4$POH, lithium siliconate and potassium siliconate, or an acid catalyst such as, e.g., $H_2SO_4$ and $CF_3SO_3H$, to form a chain siloxane polymer, which is used as a raw material for various silicone oils and silicone elastomers.

Particularly, by polymerizing the cyclotrisiloxane of the present invention in the presence of such a catalyst with a low activity as lithium siliconate, it is possible to control equilibration to the utmost, thus formation of high-molecular cyclic products being controlled. A chain siloxane polymer thus obtained is useful as an intermediate for oils containing no volatile low-molecular weight compounds.

For example, silicone oils obtained from the cyclotrisiloxane of the present invention as a starting material are expected to have an improved lubricity owing to said structural feature of the molecule, as compared with conventional dimethylsilicone oils and the like.

As described above, the cyclotrisiloxane of the present invention is useful as an intermediate for producing silicone oils and silicone rubbers of which various applications are known, and is particularly useful for producing silicone oils and silicone rubbers useful as materials for greases, cosmetics, sealing materials, paints, rubbers and the like.

DETAILED DESCRIPTION OF PREFERRED EMBODIMENTS

Figure 1:
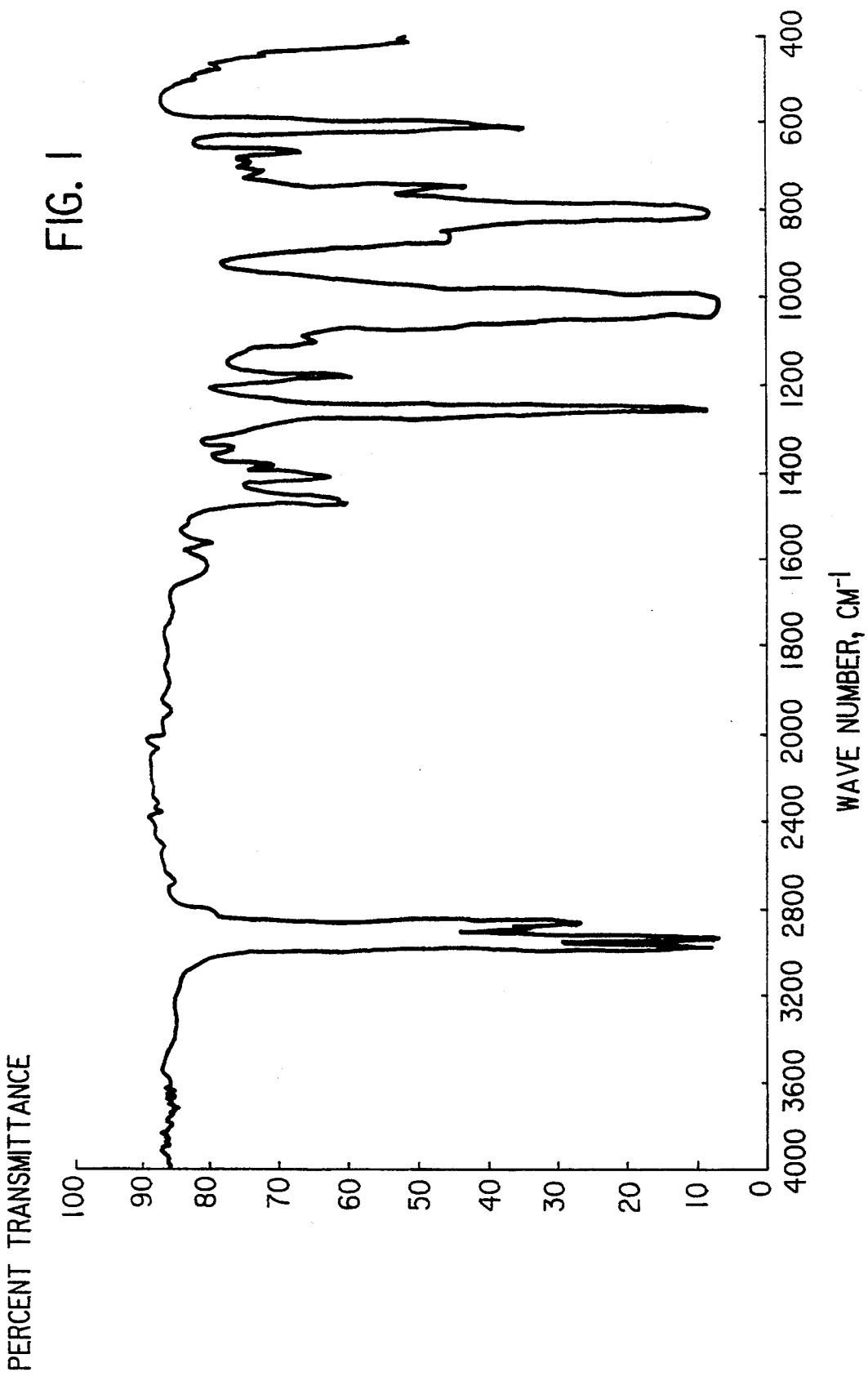
FIG. 1 is an infrared absorption spectrum chart of the cyclotrisiloxane obtained in Example 1.

In the general formula (1), the alkyl group of 1 to 3 carbon atoms expressed by $R^1$, $R^2$, $R^3$, $R^4$ and $R^5$ includes methyl, ethyl, propyl and isopropyl, particularly preferably methyl, and a hydrogen atom of these alkyl groups may be substituted by a halogen atom such as fluorine and chlorine. Further, the alkyl group $-C_nH_{2n+1}$ which can be expressed by X where n ranges from 4 to 15 includes, for example, a linear alkyl group such as butyl, pentyl, hexyl, octyl, decyl, dodecyl, and pentadecyl, and a branched alkyl group such as isobutyl, isopentyl, isooctyl, and 2-ethylhexyl.

X is preferably a cyclohexyl group or said $C_4$–$C_{12}$ alkyl group.

Production process

The cyclotrisiloxane of the present invention is obtained, for example, by reacting a disiloxanediol expressed by the general formula (2):

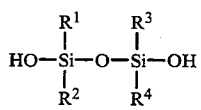

(2)

wherein $R^1$, $R^2$, $R^3$ and $R^4$ are as defined above, with a dichlorosilane expressed by the general formula (3):

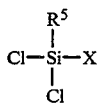

(3)

wherein $R^5$ and X are as defined above, in the presence of a catalyst.

As a catalyst used for the above reaction, preferred is a basic nitrogen-containing organic compound. The basic nitrogen-containing organic compound includes an amine compound such as triethyl amine and dimethylamine, an aromatic amine compound such as dimethylaniline, and pyridine.

These catalysts are added preferably in an amount of 1 to 6 moles, more preferably 2 to 3 moles, per mole of the dichlorosilane of the general formula (3). Reaction temperature is preferably 0° to 100° C., more preferably 30° to 70° C.

The above production process comprises, for example, preparing separately solutions of the two compounds above, adding these solutions to a catalyst-containing solution and then allowing them to react. The solvent which dissolves the disiloxanediol expressed by the general formula (2) includes preferably a polar organic solvent, which is preferably exemplified by ketones such as methylethylketone, methylisobutylketone and acetone and esters such as ethyl acetate. Further, the solvent for the dichlorosilane having the general formula (3) is an organic solvent which includes preferably an aromatic such as toluene, xylene and benzene, and a ketone such as methylisobutylketone.

Uses

Since the cyclotrisiloxane of the present invention undergoes readily a ring-opening polymerization in the presence of an alkali catalyst or an acid catalyst, it is useful as a raw material for silicone oils and silicone elastomers used in such known applications as greases, cosmetics, sealing materials, paints, various rubber materials and the like.

More particularly, the cyclotrisiloxane of the present invention has the following advantages, owing to the cyclohexyl group or the $C_4$-$C_{15}$ alkyl group linked to a silicon atom in the molecule:

(1) Since a siloxane polymer, obtained by polymerizing the cyclotrisiloxane of the present invention, is excellent in lubricity, it is useful for greases, cosmetics and the like.

(2) Since the cyclotrisiloxane of the present invention is excellent in compatibility with hydrocarbon solvents, it is useful as a raw material for paints and the like.

EXAMPLES

Example 1

A mixed solution of methylethylketone (150 g), toluene (150 g) and triethylamine (107 g) was prepared, (hereafter called Liquid A). Besides, a solution of methylhexyldichlorosilane (100 g) in toluene (150 g) (hereafter called Liquid B) and a solution of 1,1,3,3-tetramethyldisiloxane-1,3-diol (88 g) in methylethylketone (150 g) (hereafter called Liquid C) were prepared. Into the liquid A heated up to 50° C., the liquids B and C were added dropwise at almost the same dropping rate of 1 ml/min to allow methylhexyldichlorosilane and 1,1,3,3-tetramethyldisiloxane-1,3-diol to react. After dropping, the reaction liquid was agitated for 30 min. After washed with water, the reaction liquid was separated to an organic layer and an aqueous layer. After distillation of the organic layer under a reduced pressure, 106 g of a fraction at 91° C./10 mmHg was obtained.

Results of elemental analysis, infrared absorption spectrum and NMR spectrum for the product were shown below. From these results, the product compound was confirmed to be 1,1,3,3,5-pentamethyl-5-hexylcyclotrisiloxane, and its yield was 73%.

| | Elemental analysis | | |
|---|---|---|---|
| | C | H | Si |
| Calculated (%) | 45.15 | 9.65 | 28.80 |
| Found (%) | 44.83 | 9.72 | 29.05 |

(Note: Calculated value was sought in terms of $C_{11}H_{28}O_3Si_3$)

Infrared absorption spectrum
Shown in FIG. 1.
Characteristic absorption:
    1020 cm$^{-1}$: Si—O linkage
$^1$H-NMR spectrum
(Carbon tetrachloride solvent; internal standard: chloroform)
δ value (ppm)
0.13–0.50 (m, Si—CH$_3$, 15H)
1.00–1.17 (m, C—CH$_3$, 3H)
0.80–1.27 (m, CH$_2$, 10H)

Example 2

A mixed solution of methylethylketone (150 g), toluene (150 g) and triethylamine (75 g) was prepared, (hereafter called Liquid D). In addition, a solution of methyldodecyldichlorosilane (100 g) in toluene (150 g) (hereafter called Liquid E) and a solution of 1,1,3,3-tetramethyldisiloxane-1,3-diol (62 g) in methylethylketone (150 g) (hereafter called Liquid F) were prepared. Into the liquid D heated up to 50° C., the liquids E and F were added at almost the same dropping rate of 1 ml/min to allow the methylhexyldichlorosilane and 1,1,3,3-tetramethyldisiloxane-1,3-diol to react. After dropping, the mixed liquid was agitated for 30 min. After washed with water, the reaction liquid was separated into an organic layer and an aqueous layer. After distillation of the organic layer under a reduced pressure, 95 g of a fraction at 146° C./3 mmHg was obtained.

Results of elemental analysis, infrared absorption spectrum and NMR spectrum on the obtained product were shown below. From these results, the product compound was confirmed to be 1,1,3,3,5-pentamethyl-5-dodecylcyclotrisiloxane, and its yield was 72%.

| | Elemental analysis | | |
|---|---|---|---|
| | C | H | Si |
| Calculated (%) | 54.20 | 10.70 | 22.36 |
| Found (%) | 54.61 | 10.68 | 21.74 |

(Note: Calculated value in terms of $C_{17}H_{40}O_3Si_3$)

Figure 2:
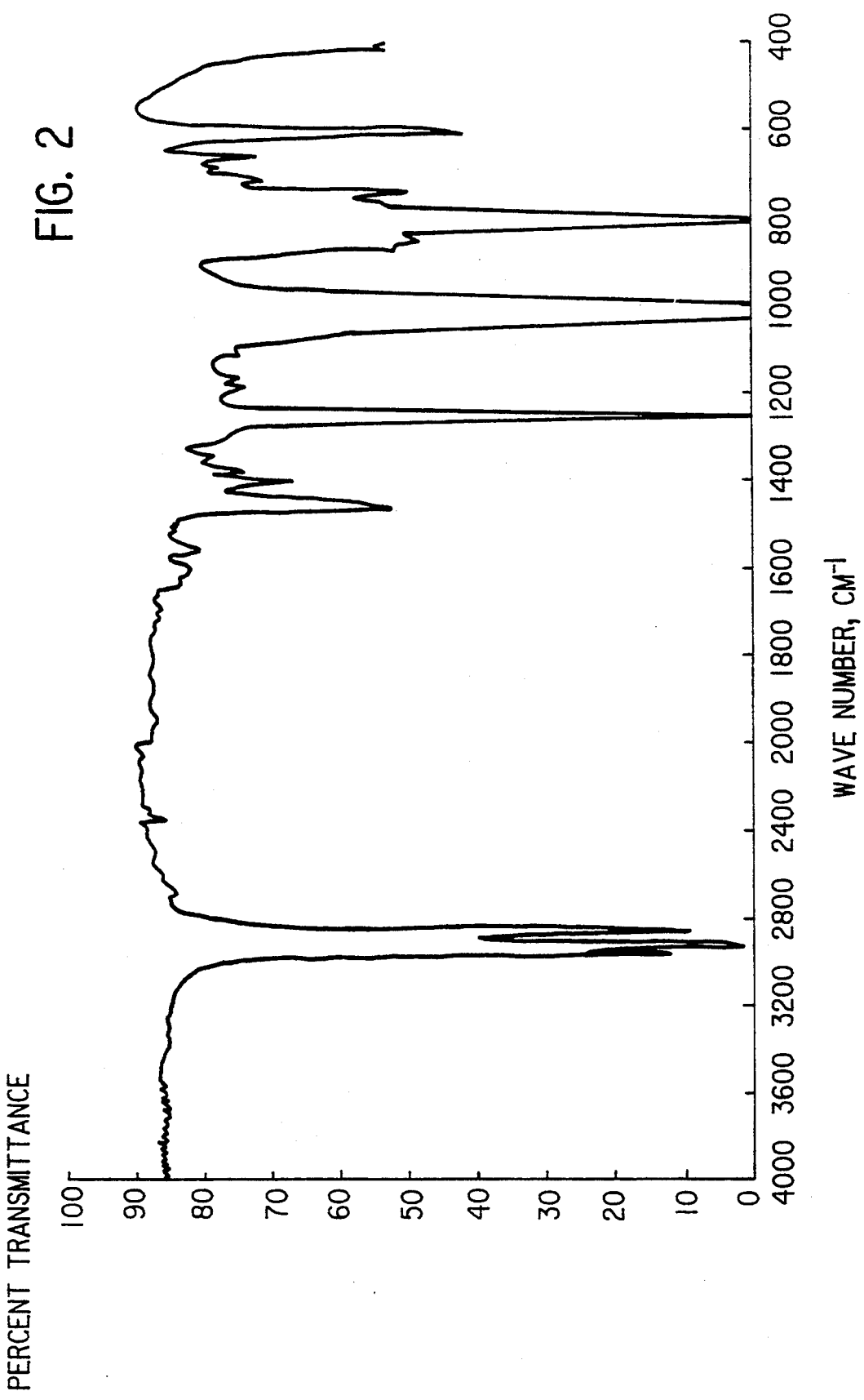
FIG. 2 is an infrared absorption spectrum chart of the cyclotrisiloxane obtained in Example 2.

Infrared absorption spectrum
Shown in FIG. 2.
Characteristic absorption:
  1020 cm$^{-1}$: Si—O linkage
$^1$H-NMR spectrum
(Carbon tetrachloride solvent; internal standard: chloroform)
δ value (ppm)
0.10–0.47 (m, Si—CH$_3$, 15H)
0.97–1.20 (m, C—CH$_3$, 3H)
1.23–1.83 (m, CH$_2$, 22H)

Example 3

Into a 4-necked flask with an internal volume of 3 liters, methylethylketone (250 g) and toluene (250 g) were charged, and then triethylamine (167 g) was dissolved therein.

To the flask two dropping funnels were installed, one of which was charged with a solution of cyclohexylmethyl dichlorosilane (150 g) dissolved in toluene (230 g). The other of the dropping funnels was charged with a solution of 1,1,3,3-tetramethyldisiloxane-1,3-diol (133 g) dissolved in methylethylketone (230 g).

Next, after heating the triethylamine solution in the flask up to 50° C., the dichlorosilane solution and the disiloxanediol solution were added dropwise from the dropping funnels at almost the same dropping rate (about 1 ml/min) and allowed to react.

After dropping, the reaction mixture was agitated for 30 minutes. The reaction product obtained was washed with water to remove a by-produced triethylamine hydrochloride. An organic layer separated was then distilled under a reduced pressure to obtain a compound (158 g) as a fraction at 112° C./26 mmHg. (Yield 72%)

Next, the compound was subjected to elemental analysis and measurements of infrared absorption spectrum and NMR spectrum. The following results were obtained.

| Elemental analysis | | | |
| --- | --- | --- | --- |
|  | C | H | Si |
| Calculated (%): | 45.47 | 9.02 | 29.00 |
| Found (%): | 45.05 | 8.96 | 29.12 |

(Note: Calculated value in terms of C$_{11}$H$_{26}$Si$_3$)

Figure 3:
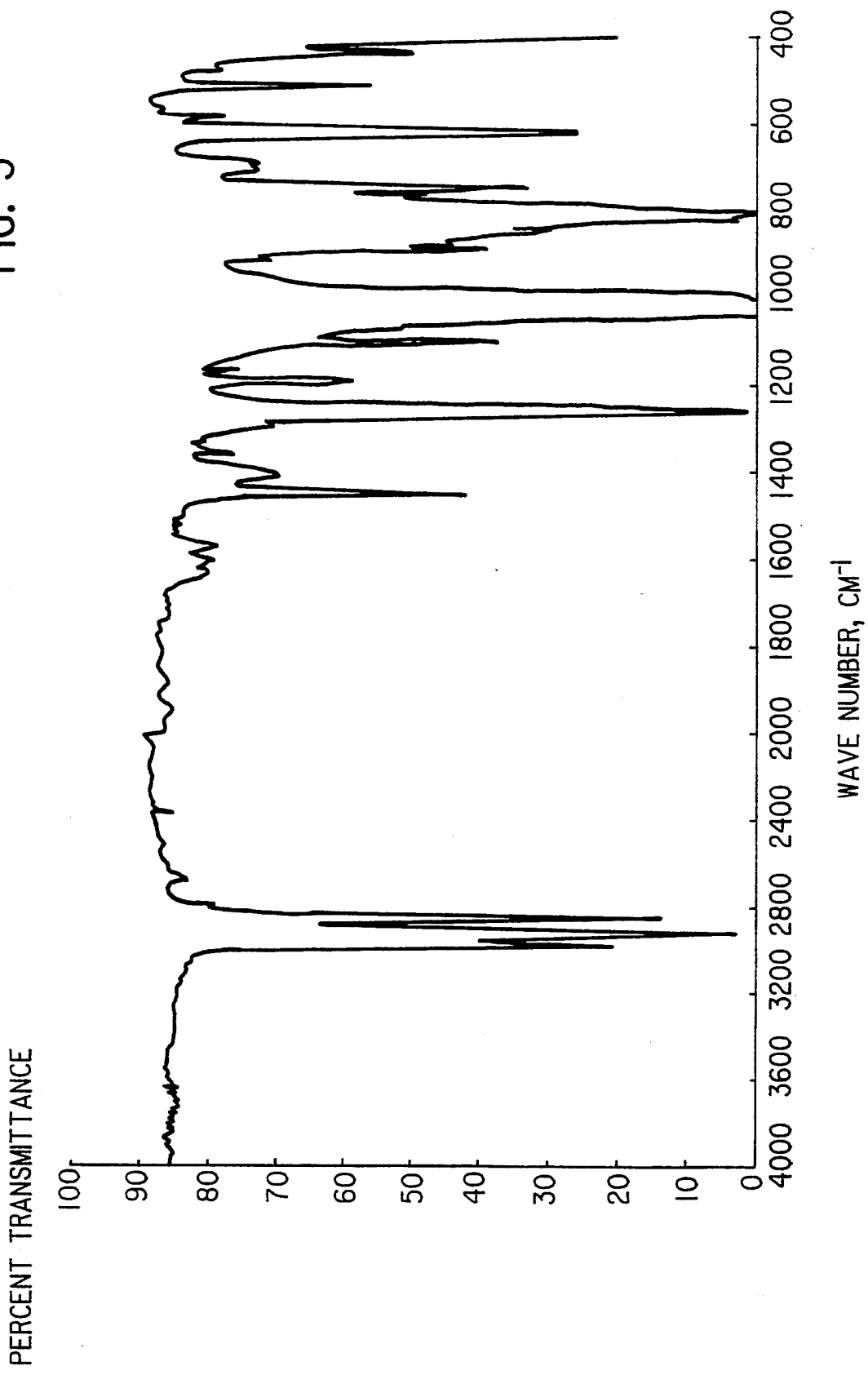
FIG. 3 is an infrared absorption spectrum chart of the cyclotrisiloxane of the present invention, synthesized in Example 3.

Infrared absorption spectrum
Shown in FIG. 3.
1020 cm$^{-1}$: (Si—O)
NMR spectrum
(Carbon tetrachloride solvent; internal standard CHCl$_3$)
δ (ppm)
0.27–0.73: (m, Si—CH$_3$, 15H)
1.20–1.40: (m, —CH$_2$—, —CH—, 11H)

From the above results, the obtained compound was confirmed to be 1,1,3,3,5-pentamethyl-5-cyclohexyl cyclotrisiloxane.

What is claimed is:

1. A cyclotrisiloxane represented by the general formula (1):

wherein R$^1$, R$^2$, R$^3$, R$^4$ and R$^5$ may be the same or different and are each a substituted or unsubstituted alkyl group having 1 to 3 carbon atoms and X is a cyclohexyl group or an alkyl group expressed by the formula:

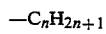

where n is an integer of 4 to 15.

2. A cyclotrisiloxane claimed in claim 1, wherein R$^1$, R$^2$, R$^3$, R$^4$ and R$^5$ are each a methyl group and X is a cyclohexyl group or an alkyl group of 4 to 12 carbon atoms.

* * * * *